(12) United States Patent
Komori et al.

(10) Patent No.: US 6,265,621 B1
(45) Date of Patent: Jul. 24, 2001

(54) PROCESS FOR PRODUCING HALOGENATED PHENOL COMPOUNDS

(75) Inventors: Hiroshi Komori, Kawanishi (JP); Kazuhiko Nishioka, Greenwich, CT (US)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/637,705

(22) Filed: Aug. 15, 2000

(30) Foreign Application Priority Data

Aug. 17, 1999 (JP) ................................. 11-230502

(51) Int. Cl.[7] .................................. C07C 39/24
(52) U.S. Cl. .................. 568/779; 568/774; 568/775; 568/709
(58) Field of Search .................... 568/709, 774, 568/775, 779

(56) References Cited

PUBLICATIONS

Yves Brunel, et al. "Iodination of Phenols and Anilines with Bis (sym–collidine) iodine (I) Hexafluorophosphate" *Tetrahedron Letters*, 1995 vol. 36, No. 45 pp. 8217–8220.
Shoji Kajigaeshi, et al. "Iodination of Phenols by Use of Benzyltrimethylammonium Dichloroiodate (1–)[1)]" *Chemistry Letters, The Chemical Society of Japan* 1987, pp. 2109–2112.
Robert Rosenfeld, et al. "Sites of iodination in recombinant human brain–derived neurotrophic factor and its effect on neurotrophic activity" *Protein Science* (1993), vol. 2, pp. 1664–1674. Cambridge University Press w/abstract.
"Selection of an iodination method" *Radioiodination Techniques–Amersham Life Science*, 1993.
Donald J. Fitzmaurice, et al. "Time–Resolved Rise of $I_2$–upon Oxidation of Iodide at Aqueous $TiO_2$ Colloid" *The Journal of Physical Chemistry*, 1993 vol. 97 No. 15 pp. 3806–3812.
Robert H. Seevers et al. "Radioiodination Techniques for Small Organic Molecules" *Chemical Reviews*, 1982, vol. 82 No. 6 pp. 575–590.
Amy L. Linsebigler, et al. "Pholocatalysis on $TiO_2$ Surfaces: Principles, Mechanisms, and Selected Results" *Chemical Reviews*, 1995 vol. 95, No. 3 pp. 735–758.

*Primary Examiner*—Johann Richter
*Assistant Examiner*—Elvis O. Price
(74) *Attorney, Agent, or Firm*—Birch, Stewart, Kolasch & Birch, LLP

(57) ABSTRACT

The present invention provides a process for producing a halogenated phenol compound represented by the general formula [II]:

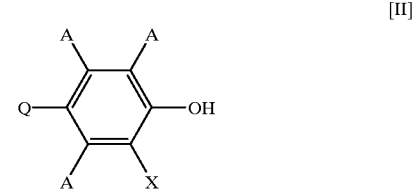

[II]

wherein Q is a monovalent organic residue, A is, the same or different, a hydrogen atom, halogen atom, —$SO_3H$ or —$SO_3Na$ group, or A at the ortho-position relative to Q may be combined with Q to form a divalent organic residue and X is a halogen atom including each isotope thereof, which comprises the step of reacting in a solvent a phenol compound represented by the general formula [I]:

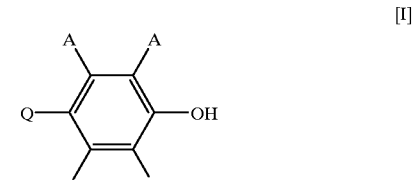

[I]

wherein X, Q and A have the same meanings as defined above, with a halide ion represented by the general formula $X^-$ wherein X has the same meanings as defined above, in the presence of a semiconductor catalyst with a photocatalytic activity under light irradiation conditions. According to the present invention, the halogenated phenol compound can be produced under moderate conditions.

7 Claims, No Drawings

PROCESS FOR PRODUCING HALOGENATED PHENOL COMPOUNDS

BACKGROUND OF THE INVENTION

1. Field of the Invention

The present invention relates to a process for producing halogenated phenol compounds. In particular, the present invention relates to a process for producing halogenated phenol compounds from phenol compounds in the presence of a halide ion ($X^-$) and a semiconductor catalyst with a photocatalytic activity under light irradiation conditions.

2. Description of the Prior Art

A halogenated phenol compound is used e.g. as an active ingredient in medicines and agrochemicals or as a synthetic intermediate of such an active ingredient. For example, a phenol compound containing a radioactive halogen atom in the molecule is widely used as a radioactive tracer used for measurement of the in vivo movement or functions of pharmaceutical chemicals etc., or as an active ingredient in diagnostic or therapeutic drug. Specifically, thyroxine containing iodine-125, for example, is used for measurement of thyroid functions; an antihuman colon cancer-derived sugar chain antigen antibody iodinated with iodine-125 is used for diagnosis of the cancer of digestive organs; an antihuman prostate acid phosphatase antibody iodinated with iodine-125 is used for diagnosis of prostate cancer; and human fibrinogen iodinated with iodine-125 is used for detection of thrombus sites.

In general, since a radioactive halogen atom is supplied stably in the state of a halide ion, a method of reacting the halide ion ($X^-$) with a phenol compound in the presence of an oxidizing agent such as chloramine T (N-chloro-4-methylbenzenesulfonamide sodium salt), Iodo-Gen™ (1,3,4,6-tetrachloro-3 α, 6 α-diphenylglycoluril), Iodo-beads™ (N-chloro-benzenesulfonamide (sodium salt) derivatized, uniform, nonporous, polystyrene beads) and hydrogen peroxide is used for producing the above-described phenol compound containing a radioactive halogen atom in the molecule.

In the method described above, however, the phenol compound to be halogenated is placed under oxidizing conditions, thus making it difficult to apply said method to those compounds which are unstable under such conditions.

Accordingly, there is a demand for development of a method of halogenation under moderate conditions applicable to those phenol compounds which are unstable under oxidizing conditions.

SUMMARY OF THE INVENTION

Under such circumstances, the present inventors have studied intensively, and have found that a halogenated phenol compound can be produced from a phenol compound in the presence of a halide ion ($X^-$) and a semiconductor catalyst with a photocatalytic activity, to reach the present invention.

That is, the present invention provides a process for producing a halogenated phenol compound represented by the general formula [II]:

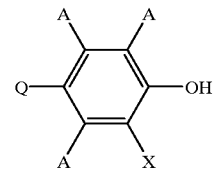

[II]

wherein Q is a monovalent organic residue, and A is, the same or different, a hydrogen atom, halogen atom, —$SO_3H$ or —$SO_3Na$ group, or A at the ortho-position relative to Q may be combined with Q to form a divalent organic residue and X is a halogen atom including each isotope thereof, which comprises the step of reacting in a solvent a phenol compound represented by the general formula [I]:

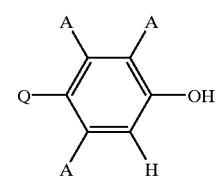

[I]

wherein X, Q and A have the same meanings as defined above with a halide ion represented by the general formula $X^-$ wherein X has the same meanings as defined above, under light irradiation conditions in the presence of a semiconductor catalyst with a photocatalytic activity (this process is referred to hereinafter as the process of the present invention.).

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

DETAILED DESCRIPTION OF THE INVENTION

The semiconductor catalyst with a photocatalytic activity to be used in the process of the present invention are semiconductor catalysts which are solid catalysts with the property that electrons in a valence band of the catalysts are excited by light. Most of the catalysts are metal oxides or metal sulfates. Specific examples of them include titanium oxide ($TiO_2$), strontium titanate ($SrTiO_3$), tungsten oxide ($WO_3$), bismuth oxide ($Bi_2O_3$), zirconium oxide ($ZrO_2$), stannum oxide ($SnO_2$), zinc oxide (ZnO) and zinc sulfide (ZnS). The semiconductor catalyst with a photocatalytic activity may have any form as long as its solid surface can receive light during its use. For example, powder, granule and ones supported on carriers by coating are available. Further, commercial available ones may also be employed.

The amount, in molar ration, of the semiconductor catalyst with a photocatalytic activity is preferably not less than that of the halide ion ($X^-$). When the concentration of the halide ion in a solution is low, the amount of the semiconductor catalyst is preferably excessive.

The light to be used in the process of the present invention may be any one which has a wavelengths at which the light can excite electrons of the semiconductor catalyst with a photocatalytic activity. For example, when titanium oxide ($TiO_2$), strontium titanate ($SrTiO_3$) or tungsten oxide ($WO_3$) is used, any light with wavelengths shorter than 388 nm may be applied. A black light, a mercury lamp, a xenon lamp and the like can be employed as a light source. By regulating the intensity of irradiation light, the rate of reaction may be regulated. Further, the wavelength used may be selected in consideration of stability of the phenol compound as the raw material and the halogenated phenol compound as the reaction product Examples of the halide ion ($X^-$) to be used in the process of the present invention include iodide ion ($I^-$), bromide ion ($Br^-$) and chloride ion ($Cl^-$). The halide ion is used in the form of its salt of a metal such as an alkali metal or of a quaternary ammonium such as tetrabutylammonium. Examples of such salts include sodium iodide (NaI), potassium iodide (KI), sodium bromide (NaBr), potassium bromide (KBr), sodium chloride (NaCl), potassium chloride (KCl). Furthermore, the halide ion also includes ions of isotopes of the halogen atoms. The isotopes may be radioactive isotopes. Examples of such isotopes include iodine-123, 125, 128, and 131, bromine-75, 76, 77, 80 and 82, chlorine-36 and 38.

The solvent to be used in the process of the present invention may be any one in which the phenol compound, which is one of the raw materials, can be dissolved with stability and a small amount of a salt of a halide can be dissolved. Examples of the solvent include dipolar aprotic solvents such as acetonitrile, dimethylformamide, dimethyl sulfoxide and the like, as well as mixed solvents thereof with water. When the raw phenol compound is water-soluble, water or a buffer may be used.

The reaction in which the reaction of the process of the present invention is conducted may be any one made of a material through which the light of a desired wavelengths can pass, and borosilicate glass reactor, a sample tube made of polypropylene and the like may be used. The light source is mounted near the reactor, and as needed, is cooled for the purpose of prevention of the temperature rise in the reactor caused by the heat from the light source. The reaction solution is stirred depending upon demand.

Q in the phenol compound of the general formula [I] used in the process of the present invention is a monovalent organic residue, where as a matter of course, there is the limitation that said organic residue does not inhibit the above-described reaction (i.e. the reaction for producing the halogenated phenol compound of the general formula [II] from the phenol compound of the general formula [I]. For example, when the phenol compound represented by the general formula [I] is a peptide as described below, the peptide may have a plural of 4-hydroxyphenyl groups each represented by the formula [A]:

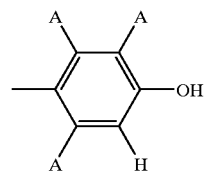

wherein A have the same meanings as defined above. In this case, some of these 4-hydroxyphenyl groups may be inert to the above-described reaction depending on the structure of Q, but at least one reactive group should be present therein. In other words, Q should have a structure in which at least one active 4-hydroxyphenyl group represented by the formula [A] is allowed to be present.

According to the process of the present invention, it may be possible to position-selectively halogenate a desired one of 4-hydroxyphenyl groups each represented by the formula [A] by regulating reaction conditions such as an amount of a halide ion, time of light irradiation and the like.

The phenol compound of the general formula [I] used in the process of the present invention includes e.g. steroid estrogen, amino acids such as tyrosine, tyronine and the like, and peptides containing these amino acids. As used herein, the term "peptide" refers to a compound having 2 or more amino acids bound therein via peptide linkages, and encompasses oligopeptides, polypeptides, proteins and the like. Such peptides may be those synthesized chemically, those isolated and purified from organisms and the like, or those prepared through genetic engineering techniques, cell engineering techniques and the like. Specifically, examples may include rose bengal, bromosulfophthalein, estradiol, estrone, estriol, equilin, equilenin, ethynylestradiol, thyronine, triiodothyronine, insulin, glucagon, somatostatin, somatomedin C, β-endorphin, neurotensin, neurokinin, gastrin, calcitonin, angiotensin I, angiotensin II, erythropoietin, vasopressin, ACTH (adrenocorticotrophic hormone), EGF (epithelial growth factor), IL-1 (interleukin I), TNFα (tumor necrosis factor α), α-bungarotoxin, endoserine-1, endoserine-3, IGF-2 (insulin-like growth factor), interferon, BDNF (brain-derived neurotropnic factor), HGF (hepatocyte growth factor), trypsin, anti-TSH (thyrotropin) antibody, anti-ferritin antibody, anti-prolactin antibody, anti-ACTH (adrenocorticotrophic hormone) antibody, anti-LH (human luteinizing hormone) antibody, antihuman breast cancer-derived antigen antibody, antihuman cancer embryonal antigen antibody, human cancer embryonal antigen, antihuman ovary cancer-derived antigen antibody, antihuman colon cancer-derived sugar chain antigen antibody, antihuman nerve-specific enolase antibody, antihuman prostate acid phosphatase antibody, anti-α-fetoprotein antibody, anti-procollagen-III-peptide antibody, anti-hepatitis A virus antibody, anti-hepatitis B virus surface antigen antibody, hepatitis B virus surface antigen, anti-hepatitis B virus core antigen antibody, anti-hepatitis B virus e antigen antibody, human immunoglobulin E, anti-mouse immunoglobulin G antibody, anti-rat immunoglobulin G antibody, antihuman immunoglobulin G antibody, anti-rabbit immunoglobulin G antibody and the like.

The reaction in the process of the present invention may also be conducted further in the presence of an electron acceptor other than the raw materials. Preferable electron acceptors are ions of metals whose ionization tendencies are greater than that of hydrogen atom. In particular, when titanium oxide ($TiO_2$), strontium titanate ($SrTiO_3$), tungsten oxide (WO₃), bismuth oxide (Bi₂O₃), zirconium oxide (ZrO₂) or Stannum oxide (SnO₂) is used as the semiconductor catalyst with a photocatalytic activity, a silver ion (Ag⁺) is preferred. Concretely, the silver ion is used as salts such as silver sulfate (Ag₂SO₄). The metal ion as the electron acceptor is preferably used in an amount, in molar ratio, as much as twice or more that of the halide ion (X⁻).

The reaction in the process of the present invention may be stopped by merely terminating the light irradiation. The reaction rate may also be easily controlled by selecting the quantity of light. The wavelength may also be selected. After the completion of the reaction, the desired halogenated phenol compound may be obtained by subjecting the reaction solution to column chromatography or HPLC after, if necessary, separating (for example, filtrating off) the semiconductor catalyst with a photocatalytic activity.

According to the process of the present invention, a halogenated phenol compound can be produced from a phenol compound under moderate conditions. The process of the present invention is useful particularly in the field of production of labeled compound which should be synthesized in high purities and in high specific radioactivities from small amounts of radioactive halogen atom supplied in the state of a halide ion. Further, the process of the present invention may also be useful for position-selective halogenation of a phenol compound, which is difficult in the prior art method.

EXAMPLE

Hereinafter, the present invention will be concretely explained with reference to the Example. The invention, however, is not limited to the example.

Example 1

Human brain-derived neurotropnic factor (BDNF) is composed of 119 amino acids containing tyrosine residues at the 52-, 54-, 63- and 86-positions from the N-terminal thereof, and when iodine is introduced into a tyrosine residue at the 63-position, BDNF activity is maintained (Protein Science, 2, 1664–1674, 1993)

A solution (100 μl) of BDNF (purchased from Funakoshi) (10 μg, 0.740 nmol) in PBS was put to a polypropylene sample tube (1.5 ml, Diayatron Co., Ltd.). Then, granular titanium oxide (TiO₂, Ishihara Sangyo Kaisha, Ltd.) (0.14 mg, 1.75 μmol), silver sulfate (1.14 μg, 3.65 nmol in 2 μl aqueous solution), sodium iodide [¹²⁵I] (37.0 MBq, 0.46 nmol in 10 μl aqueous solution, produced by Amersham), sodium iodide (41 ng, 0.27 nmol in 1 μl aqueous solution) were added thereto. A black light (5 W. NEC Co.) was on for 10 minutes at room temperature. The light source was arranged 10 cm over the reaction vessel. After the light was turned off, 113 μl of the reaction solution was subjected to radio high performance liquid chromatography described below.
(Conditions for Radio High Performance Liquid Chromatography) Column: VYDAC PROTEIN C4, 4.6 mmID×25 cm, 5 μm, produced by Separations Group.
Mobile Phase A; 0.1% aqueous trifluoroacetic acid, B; acetonitrile/0.1% aqueous trifluoroacetic acid=9/1 (v/v).

After a mixed solvent (A/B=80/20 (v/v)) was passed for 45 minutes, the mixed solvent was passed with an increasing concentration of B at a rate of 20% B/hour for 60 minutes [final composition: A/B=60/40 (v/v)].
Flow rate: 1.0 ml/min.

Detector: Radioactivity detector (Radio Analyzer RLC-551, Aloka Co., Ltd.).
Retention time of [63Tyr-¹²⁵I] BDNF: 95.6 minutes.

By the retention time in chromatography, [63Tyr-¹²⁵I] BDNF was identified. The radiochemical purity of [63Tyr-¹²⁵I] BDNF was 98%, and the yield thereof based on sodium iodide [¹²⁵I] was 23%. On the chromatogram in chromatography, there was no peak corresponding to a decomposed product of [63Tyr-¹²⁵I] BDNF. The ratio of formation thereof based on the peak ratio on the chromatogram was 85% for [63Tyr-¹²⁵I] BDNF and 15% for [86Tyr ¹²⁵I] BDNF. On the chromatogram, there was no peak corresponding to BDNF having ¹²⁵I introduced into both 63Tyr and 86Tyr or to BDNF having ¹²⁵I introduced into either 52Tyr or 541Tyr.

According to the present invention, the halogenated phenol compound can be produced under moderate conditions.

What is claimed is:

1. A process for producing a halogenated phenol compound represented by the general formula [II]:

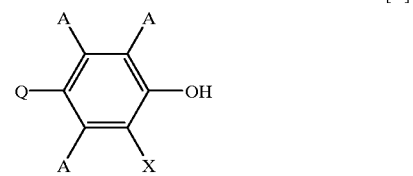

[II]

wherein Q is a monovalent organic residue, A is, the same or different, a hydrogen atom, halogen atom, —SO₃H or —S₃Na group, or A at the ortho-position relative to Q may be combined with Q to form a divalent organic residue and X is a halogen atom including each isotope thereof, which comprises the step of reacting in a solvent a phenol compound represented by the general formula [I]:

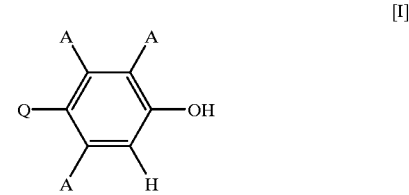

[I]

wherein X, Q and A have the same meanings as defined above, with a halide ion represented by the general formula X⁻ wherein X has the same meanings as defined above, in the presence of a semiconductor catalyst with a photocatalytic activity under light irradiation conditions.

2. The process according to claim 1, wherein the halide ion is halide ion being a radioisotope.

3. The process according to claim 1, wherein the halide ion is an iodide ion (I⁻), a bromide ion (Br⁻) or a chloride ion (Cl⁻).

4. The process according to claim 1, wherein the semiconductor catalyst with a photocatalytic activity is at least one kind selected from the group consisting of titanium oxide (TiO₂), strontium titanate (SrTiO₃), tungsten oxide (WO₃), bismuth oxide (Bi₂O₃), zirconium oxide (ZrO₂), tin oxide (SnO₂), zinc oxide (ZnO) and zinc sulfide (ZnS).

5. The process according to claim 1, wherein the reaction is carried out further in the presence of a silver ion.

6. The process according to claim 1, wherein the phenol compound represented by the general formula [I] is a peptide containing tyrosine as a constituent amino acid.

7. A process for halogenation of a phenol compound by introducing a halogen atom into an ortho-position relative to a phenolic hydroxyl group having a hydrogen atom at the ortho-position, which comprises the step of reacting in a solvent under light irradiation conditions in the presence of a semiconductor catalyst with a photocatalytic activity.

* * * * *